United States Patent
Pierce et al.

(10) Patent No.: US 6,710,221 B1
(45) Date of Patent: Mar. 23, 2004

(54) ABSORBENT ARTICLES INCORPORATING COLOR CHANGE GRAPHICS

(75) Inventors: Joseph Earl Pierce, Appleton, WI (US); Thomas Michael Lager, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/587,003

(22) Filed: Jun. 5, 2000

Related U.S. Application Data

(60) Provisional application No. 60/139,282, filed on Jun. 15, 1999.

(51) Int. Cl.$^7$ ................................................. A61F 13/15
(52) U.S. Cl. ............................................................. 604/361
(58) Field of Search ................................. 604/361, 364, 604/385.01, 385.21, 385.23, 386, 387, 396; 116/200, 206, 207, 208; 128/886

(56) References Cited

U.S. PATENT DOCUMENTS

| | | |
|---|---|---|
| 2,787,238 A | 4/1957 | Luce |
| 3,004,895 A | 10/1961 | Schwartz |
| 3,675,654 A | 7/1972 | Baker et al. |
| 3,702,610 A | 11/1972 | Sheppard et al. |
| 3,759,261 A | 9/1973 | Wang |
| 3,898,172 A | 8/1975 | Reif et al. |
| 3,918,454 A | 11/1975 | Korodi et al. |
| 3,952,746 A | 4/1976 | Summers |
| 4,022,211 A | 5/1977 | Timmons et al. |
| 4,192,311 A | 3/1980 | Felfoldi |
| 4,231,370 A | 11/1980 | Mroz et al. |
| 4,249,532 A | 2/1981 | Polansky et al. |
| 4,287,153 A | 9/1981 | Towsend |
| 4,292,916 A | 10/1981 | Bradley et al. |
| 4,327,731 A | 5/1982 | Powell |
| 4,507,121 A | 3/1985 | Leung |
| 4,581,772 A | 4/1986 | Smith |
| 4,662,875 A | 5/1987 | Hirotsu et al. |
| 4,663,220 A | 5/1987 | Wisneski et al. |
| 4,704,116 A | 11/1987 | Enloe |

(List continued on next page.)

FOREIGN PATENT DOCUMENTS

| | | |
|---|---|---|
| DE | 3810473 A1 | 10/1989 |
| EP | 0021492 A1 | 1/1981 |
| EP | 0148115 A1 | 7/1985 |
| EP | 0203715 A2 | 12/1986 |
| EP | 0217032 A2 | 4/1987 |

(List continued on next page.)

OTHER PUBLICATIONS

Patent Abstracts of Japan 10108877 A: Description of Uni Charm Corp., "DISPOSABLE DIAPER OF BRIEFS TYPE".

(List continued on next page.)

Primary Examiner—Weilun Lo
Assistant Examiner—Michele Kidwell
(74) Attorney, Agent, or Firm—Thomas M. Gage; John L. Brodersen

(57) ABSTRACT

A disposable absorbent article such as a training pant includes active graphics that can change color during use and can provide an interactive training aid. The active graphics in particular embodiments can comprise moisture sensitive color change compositions that disappear from view or blend in with background graphics upon activation. In particular embodiments, the active graphics comprise at least two compositions that have different post-activation colors.

26 Claims, 7 Drawing Sheets

U.S. PATENT DOCUMENTS

| | | |
|---|---|---|
| 4,705,513 A | 11/1987 | Sheldon et al. |
| 4,735,622 A | 4/1988 | Acuff et al. |
| 4,743,238 A | 5/1988 | Colon et al. |
| 4,776,800 A | 10/1988 | Anderson |
| 4,810,562 A | 3/1989 | Okawa et al. |
| 4,812,053 A | 3/1989 | Bhattacharjee |
| 4,834,733 A | 5/1989 | Huntoon et al. |
| 4,895,567 A | 1/1990 | Colon et al. |
| 4,903,254 A | 2/1990 | Haas |
| 4,909,879 A | 3/1990 | Ball |
| 4,931,051 A | 6/1990 | Castello |
| 4,940,464 A | 7/1990 | Van Gompel et al. |
| 4,987,849 A | 1/1991 | Sherman |
| 5,035,691 A | 7/1991 | Zimmel et al. |
| 5,045,283 A | 9/1991 | Patel |
| 5,046,272 A | 9/1991 | Vogt et al. |
| 5,053,339 A | 10/1991 | Patel |
| 5,058,088 A | 10/1991 | Haas et al. |
| 5,066,711 A | 11/1991 | Colon et al. |
| 5,078,708 A | 1/1992 | Haque |
| D323,920 S | 2/1992 | Pitts |
| 5,089,548 A | 2/1992 | Zimmel et al. |
| 5,104,116 A | 4/1992 | Pohjola |
| 5,130,290 A | 7/1992 | Tanimoto |
| 5,133,087 A | 7/1992 | Machida et al. |
| 5,167,652 A | 12/1992 | Mueller |
| 5,197,958 A | 3/1993 | Howell |
| 5,224,405 A | 7/1993 | Pohjola |
| 5,226,992 A | 7/1993 | Morman |
| 5,286,543 A | 2/1994 | Ungpiyakul et al. |
| 5,354,289 A | 10/1994 | Mitchell et al. |
| H1376 H | 11/1994 | Osborn, III et al. |
| 5,364,132 A | 11/1994 | Haas et al. |
| 5,389,093 A | 2/1995 | Howell |
| 5,411,295 A | 5/1995 | Bates et al. |
| 5,435,010 A | 7/1995 | May |
| 5,458,590 A | 10/1995 | Schleinz et al. |
| 5,683,752 A | 11/1997 | Popp et al. |
| 5,766,212 A | 6/1998 | Jitoe et al. |
| 5,766,389 A | 6/1998 | Brandon et al. |
| 5,897,541 A | 4/1999 | Uitenbroek et al. |
| 5,897,546 A | 4/1999 | Kido et al. |
| 6,045,543 A | 4/2000 | Pozniak et al. |
| 6,075,178 A | 6/2000 | La Wilhelm et al. |
| 6,238,519 B1 | 5/2001 | Jones et al. |
| 6,297,424 B1 * | 10/2001 | Olson et al. ............... 604/361 |
| 6,307,119 B1 * | 10/2001 | Cammarota et al. ........ 604/361 |

FOREIGN PATENT DOCUMENTS

| | | |
|---|---|---|
| EP | 0286543 A2 | 10/1988 |
| EP | 0776645 A1 | 6/1997 |
| EP | 0813850 A2 | 12/1997 |
| FR | 2541872 A3 | 9/1984 |
| FR | 2559037 A1 | 8/1995 |
| GB | 2022423 A | 12/1979 |
| JP | 58174601 A | 10/1983 |
| JP | 1075980 A | 3/1989 |
| JP | 9140742 | 6/1997 |
| WO | WO 8604219 A1 | 7/1986 |
| WO | WO 8700945 A1 | 2/1987 |
| WO | WO 95800099 A1 | 1/1995 |
| WO | WO 00/35401 A1 | 6/2000 |
| WO | WO 00/76443 A1 | 12/2000 |
| WO | WO 01/21126 A1 | 3/2001 |

OTHER PUBLICATIONS

Patent Abstracts of Japan 11104172 A: Description of Uni Charm Corp., "DISPOSABLE PANTS TYPE DIAPER".

Patent Abstracts of Japan 2000000266 A: Description of Oji PaPer Co. Ltd., "PRINTING OF ABSORPTIVE WEARING ARTICLE AND ABSORPTIVE WEARING ARTICLE SUBJECTED TO PRINTING".

Patent Abstracts of Japan 2001170108 A2: Description of Crecia Corp., "PERFECT BRIEF SHAPED PAPER DIAPER".

* cited by examiner

ABSORBENT ARTICLES INCORPORATING COLOR CHANGE GRAPHICS

This application claims priority under 35 USC 119(e) from U.S. Provisional Application No. 60/139,282, filed on Jun. 15, 1999.

BACKGROUND OF THE INVENTION

The present invention relates to absorbent articles, and more particularly to absorbent articles having active graphics that can change color during use.

The toilet training process may incorporate a wide variety of different aspects, including many training techniques and training aids that may be used by parents and caregivers, hereinafter simply referred to as caregivers. One aspect of the total toilet training process is the change from diapers to training pants to help the child understand that he or she should now use the toilet just like adults. Another aspect of the total toilet training process includes caregiver instruction as a positive encouragement and reinforcement to the child that he or she should now be using a toilet instead of diapers. Although the use of training pants and positive encouragement from the caregiver has been helpful in the toilet training process, there is still much room for improvement. Specifically, caregivers are still searching for easier and quicker ways to guide their children successfully through the toilet training process.

Many caregivers have difficulty in determining the readiness of a child to begin the toilet training process, and underestimate the difficulty of teaching the toilet training process to young children. If a child does not respond to an initial toilet training instruction or introduction, the caregiver can be at a loss for finding techniques, methods, or teaching tools to encourage the child to master the art of toilet training. Thus, while various teaching tools such as books, videotapes, charts with stickers, personalized toilets, and interactive toilet training kits are available, there remains a need for new and improved educational and motivational mechanisms to facilitate the toilet training process.

SUMMARY OF THE INVENTION

In response to the discussed deficiencies associated with prior absorbent garments, an absorbent article has been developed that provides toilet training aid benefits through the use of interactive graphics, which can include one or more active graphics. Certain graphics are referred to as "active" because they are constructed to "disappear" or "appear" from view, such as when the child has an accident and the active graphic is contacted with urine or upon prolonged exposure to the environment. The interactive wetness indicating graphics can also include one or more permanent graphics which can, in combination with the active graphics, provide a story line that is useful to teach the child important lessons regarding toilet training.

Hence, in one embodiment, the invention concerns an absorbent article that includes an outer cover having in interior surface and an opposite exterior surface, where the outer cover has a first color. The absorbent article also includes an absorbent assembly disposed on the interior surface of the outer cover. An active graphic of the absorbent article is disposed on the outer cover and comprises a color change composition. The active graphic has a pre-activation color different from the first color and a post-activation color substantially the same as the first color. As used herein, the phrase "post-activation color substantially the same" as another color includes the same color, visually similar colors and clear.

In another embodiment, the absorbent article can also include a background graphic disposed on the outer cover and having a second color different from the outer cover first color. The active graphic can have a pre-activation color different from the first color and the second color and a post-activation color substantially the same as the second color.

In a further embodiment, the active graphic can comprise at least two color change compositions that have a pre-activation color different from the outer cover first color and the background graphic second color. At least one of the color change compositions can have a post-activation color substantially the same as the first color, and at least one of the color change compositions can have a post-activation color substantially the same as the second color.

In yet another embodiment, the active graphic can comprise a first active graphic and a second active graphic that are disposed on the outer cover and that comprise color change compositions. The first active graphic can have a pre-activation color different from the outer cover first color and the background graphic second color and a post-activation color substantially the same as the second color. The second active graphic can have a pre-activation color substantially the same as the first color and a post-activation color substantially the same as the second color.

In another embodiment, the invention concerns an absorbent article that includes an outer cover having an interior surface, an opposite exterior surface and a first color. An absorbent assembly is disposed on the interior surface of the outer cover. An active graphic of the absorbent article is disposed on the outer cover and comprises a color change composition providing a pre-activation color substantially the same as the first color and a post-activation color different from the first color. This embodiment provides an active graphic that appears over time.

The term "active graphic" as used herein refers to an appearing graphic, a fading graphic, or a combination of appearing and fading graphics. The term "appearing graphic" is used herein to refer to a graphic that becomes visible or becomes significantly more visible when exposed to urine, or that becomes visible or becomes significantly more visible with the passage of time when exposed to the environment but not exposed to urine. Conversely, the term "fading graphic" is used herein to refer to a graphic that becomes invisible or becomes significantly less visible when exposed to urine, or that becomes invisible or becomes significantly less visible with the passage of time when exposed to the environment but not exposed to urine.

In any of the above-referenced and further embodiments of the absorbent article, the active graphics can comprise moisture sensitive color change compositions. The term "moisture sensitive color change composition" refers to an active graphic that changes color from a pre-activation color to a post-activation color when exposed to liquid such as urine. Suitable compositions can comprise an ink, an adhesive, or the like that changes color when exposed to an aqueous solution such as urine. Such active graphics can comprise a fading graphic or an appearing graphic, whereupon the color change composition can be adapted to blend in with a background or surrounding color, either before or after exposure to the aqueous solution. Suitable compositions of this color-change type are available from a variety of commercial vendors, such as such as a pH-change/color-change hot melt adhesive available from Findley Adhesives, Inc. of Wauwatosa, Wis., USA. Other potentially suitable means by which a color may be made to appear or disappear, or by which one color may be converted or appear to be converted into another, include chemical reactions resulting from interaction with urine or from dissolution of spatially separated reactants into urine. Such reactions may include but are not limited to color changes of pH indicating molecules, formation or degradation of colored complexes, the action of one or more enzymes that occur naturally in urine on colored molecules or precursors thereof, oxidation and/or reduction reactions, and reactions of two or more components that are spatially separated within a product, at least one of which is soluble in urine, and which upon contact, react to create or destroy a colored region. Further examples of potentially suitable means to achieve color changes include the pre-combination of two colors to form a blended color, after the wetting of which one color component may be solubilized or destroyed to leave only the second color component visible, and molecules that exhibit different color properties in crystalline and dissolved states.

Other active graphics of the absorbent article can comprise a fading graphic which is formed from a composition such as an ink that is soluble in aqueous solutions such as urine. The composition can be positioned in the absorbent article so that it becomes wet and dissolves when the product is insulted with liquid. Once dissolved, the composition washes away from the outer cover and is obscured by the outer cover. As a result, the active graphic seems to disappear from view.

Suitable urine-soluble inks are available from a variety of commercial vendors, such as Sun Chemical Corp. of Philadelphia, Pa., USA under the trade designation AQUA DESTRUCT. Particular urine-soluble compositions are disclosed in U.S. Pat. No. 4,022,211 issued May 10, 1977 to Timmons et al., which is incorporated herein by reference. The ink color can be selected to provide a pleasing appearance and graphic impact, including fading rapidly upon contact with liquid. To facilitate rapid fading, the fading graphics can comprise line drawings having a line width of from about 1 to about 2 millimeters. Thus, the active graphic can comprise pH sensitive inks, fugitive inks, colored absorbent particles, hydratable salts, moisture sensitive films, enzymes, heat sensitive inks and dyes, or the like.

Fading graphics can simply disappear from view, relative to the exterior surface of the outer cover. For example, fading object graphics can be made to disappear into a permanent background graphic. Representative examples include an object graphic such as yellow fish disappearing or fading into a background graphic such as blue water or green weeds; an object graphic such as pink flowers fading into a background graphic such as a green lawn; an object graphic such as lavender sand toys fading into a background graphic such as tan sand; an object graphic such as pink sea shells fading into a background graphic such as tan sand; an object graphic such as small animals fading into a background graphic such as a jungle scene; an object graphic such as frogs fading into a background graphic such as water lilies; an object graphic such as green toys fading into a background graphic such as a yellow floor or blanket area; an object graphic such as pink angels fading into a background graphic such as blue clouds; an object graphic such as a red bone fading into a background graphic such as the inside of a dog's dish; an object graphic such as a cat's yellow yarn balls fading into a background graphic such as a green checkered floor; an object graphic such as a toy car disappearing from a background graphic such as a road; or the like.

The active graphic can also be configured to appear over time due to exposure to the environment. In particular, the active graphic can be responsive to time intervals, temperature levels, oxygen levels, or the like, and combinations thereof. Various visual indicators that appear over time in response to particular conditions are disclosed in U.S. Pat. No. 5,058,088 issued Oct. 15, 1991 to Haas et al.; U.S. Pat. No. 5,053,339 issued Oct. 1, 1991 to Patel; U.S. Pat. No. 5,045,283 issued Sep. 3, 1991 to Patel; U.S. Pat. No. 4,987,849 issued Jan. 29, 1991 to Sherman; U.S. Pat. No. 4,903,254 issued Feb. 20, 1990 to Haas; U.S. Pat. No. 4,812,053 issued Mar. 14, 1989 to Bhattacharjee; and U.S. Pat. No. 4,292,916 issued Oct. 6, 1981 to Bradley et al.; all of which are incorporated herein by reference. An active graphic that appears over time can be applied to the product when use is initiated, activated when use is initiated such as by removal of a protective cover layer, formed as an integral component of the product, or the like.

In contrast to active graphics, the term "permanent graphic" is used herein to refer to a graphic that does not substantially change its degree of visibility when the absorbent article is insulted with urine and when the absorbent article is exposed to the environment, in simulated use conditions. The change in visibility of a graphic or a portion of a graphic can be determined based on a person's observation of the graphic before and after the article containing the graphic is exposed to liquid. For purposes hereof, an article is exposed to liquid by immersing the article completely in an aqueous solution containing 0.9 weight percent sodium chloride, used at room temperature ($\cong 23°$ C.), for a period of twenty minutes. After 20 minutes the product is removed from the aqueous solution and placed on a TEFLON™ coated fiberglass screen having 0.25 inch openings, which is commercially available from Taconic Plastics Inc., Petersberg, N.Y., USA, which in turn is placed on a vacuum box and covered with a flexible rubber dam material. A vacuum of 3.5 kilopascals (0.5 pounds per square inch) is drawn in the vacuum box for a period of 5 minutes, after which the article is removed and observed. The person with normal or corrected vision of about 20–20 should make the observations from a distance of 1 meter in an environment providing 30 footcandles (320 Lux) of illumination. Changes in the visibility of the graphic should be identified, and distinguished where necessary from changes in the color of other materials such as fluff pulp within an absorbent assembly. Desirably, the permanent graphic can be configured so that the entire graphic also does not substantially change its appearance, size or shape when the product is insulted with liquid or exposed to the environment.

The graphics of the absorbent article can include object graphics, including but not limited to character graphics, inanimate objects, background graphics, or the like. The term "character graphic" is used herein to refer to a graphic containing an anthropomorphous image, and in particular an image having or suggesting human form or appearance which ascribes human motivations, characteristics or behavior to inanimate objects, animals, natural phenomena, cartoon characters, or the like. Ideally the character graphic would be suitable for children's underwear and could be utilized to motivate children to wear the pants and use a potty or toilet. To that end, the character graphics can be associated with popular characters in the media, advertising or well known in a particular culture. Ideally they are characters that the child or caregiver care about and want to identify with. Ideally the child can imagine himself or herself taking the place of the character. Suitable character graphics can include animals, people, inanimate objects, natural phenomena, cartoon characters, or the like that can or can not be provided with human features such as arms, legs, facial features or the like. The character graphics can comprise permanent graphics, active graphics, or both permanent and active graphics.

The term "background graphic" is used herein to refer to a graphic that is disposed adjacent to, around, near or surrounding one or more active graphics. The background graphics can comprise permanent graphics, active graphics, or both permanent and active graphics, and can comprise one or a plurality of colors. Desirably, the background graphic is related in subject matter to the active graphic.

As used herein, the phrase "related in subject matter" refers to the situation where the subject matter of one graphic is the same as or is linked to the subject matter of another graphic. The subject matter relationship can be between two or more text messages, between two or more pictorial images, or between a combination of one or more text messages and one or more pictorial images. The term "text message" means a graphic consisting of one or more alphanumeric symbols, and the term "pictorial image" means a graphic consisting of one or more pictures. The terms "text image" and "pictorial image" are mutually exclusive as used herein. The general term "graphic" is used herein to mean any design, pattern, or the like that is or becomes visible on an absorbent article, and specifically includes text messages that consist of one or more alphanumeric symbols, pictorial images that consist of one or more pictures, and combinations thereof.

By way of example, two pictorial images are considered related in subject matter where the images are identical; separately illustrate different sizes, shapes, colors of a common object; each illustrate one and the other of two objects that are commonly associated with one another, such as the moon and stars, a body of water and water toys, a sandbox and suitable toys, a baseball bat and ball, a barn and animals, or the like; illustrate different items used in a particular activity, such as a sporting activity, a gardening activity or the like; jointly illustrate geometrically mating or engaging elements such as a triangle and a triangularly-shaped aperture, or two halves of a zipper; each illustrate one part of a multipart picture; or the like. Similarly, two text messages are considered related in subject matter where the messages: are identical; jointly form a sentence, thought, or action such as "jump" and "up"; each refer to one and the other of two items that are commonly associated with one another, such as "bat" and "ball," "Big" and "Kid," "Big" and "Girl," or "Big" and "Boy"; jointly present a question and answer; or the like. Likewise, a text message and a pictorial image are considered to be related in subject matter where the text names, defines or describes the image; or the like.

In use, the active graphic can appear or fade when an accident occurs and urine comes into contact with the active graphic. Desirably, the active graphic appears or fades in about 3 minutes or less, particularly in about 1 minute or less, and more desirably in about 20 seconds or less, when the absorbent article is insulted with 200 milliliters or more of urine, and more desirably about 40 to about 60 milliliters or more of urine.

The changed condition of the graphic presents a tool for the caregiver to interact with the child and explain why the graphic changed. This is particularly useful at the stage of toilet training where the child is being taught to be aware of going potty and the need to use the bathroom. The combination of active graphics and related permanent graphics are believed to make children more interested in the toilet training process and therefore lead to enhanced results.

Permanent graphics can be positioned anywhere on the outer cover, and in particular embodiments can desirably be positioned in the front waist region along or near the longitudinal centerline of the product. Particular arrangements for permanent and wetness indicating graphics are disclosed in U.S. patent application Ser. No. 09/333,223, filed on Jun. 15, 1999 by Cammarota et al. and titled "Absorbent Articles Having Wetness Indicating Graphics Incorporating A Training Zone" and U.S. patent application Ser. No. 09/333,222, filed on Jun. 15, 1999 by Olson et al. and titled "Absorbent Articles Having Wetness Indicating Graphics Providing An Interactive Training Aid."

The active graphics can but need not necessarily be positioned closer to the transverse centerline of the product than the permanent graphics. In particular embodiments, the active graphics are positioned between the transverse centerline of the product and the permanent graphic so as to be properly focussed and not hidden from view during use. Locating the active graphics in the crotch region of the product, near the target spot for urination, may also assist with rapid exposure of the fading graphic to urine upon insult. It is desirable to locate active graphics that are moisture sensitive on the area of the outer cover that is most likely to experience wetness during the first void. Of course, alternative positioning of the permanent and active graphics are possible, such as the permanent graphic in the crotch region and the active graphic in one of the waist regions, both permanent and active graphics in one or both of the waist regions and/or the crotch region, or the like. The active graphics can but need not necessarily be positioned on one or more sides of the permanent graphics, such as "floating" under the permanent graphic. Alternatively, the permanent graphic can surround the active graphic and vice versa.

In one particular embodiment, all of the active object graphics are located in a distinct active graphic region where the child can focus attention. The active graphic region suitably has a length dimension measured parallel to the longitudinal centerline of about 10 centimeters, more particularly about 9 centimeters, and a width dimension measured parallel to the transverse centerline of about 6 centimeters. The active graphic region can, for instance, be spaced from the first end edge of the product by approximately 13 to 16 centimeters.

There can be one or more active object graphics. It is believed desirable to use a plurality of active object graphics in order provide the greatest impact to the child. In particular embodiments, a training pant comprises 3 or more active object graphics, particularly from 4 to 8, such as 5 arranged in a 2-1-2 pattern.

The size of the active object graphics can depend in part on their number and type. It is generally preferred that the active object graphics have a size of at least about 1.5 by 1.5 centimeter and less than about 3 by 3 centimeters, and particularly at least about 1.8 by 1.8 centimeter and less than about 2.5 by 2.5 centimeters.

The overall size of the permanent graphic can be significantly larger than the overall size of each discrete active graphic. In particular embodiments, for instance, the permanent graphic has a size measured by overall surface area that is at least twice as large, and more particularly at least three times as large, as the size of a single active graphic. The maximum length dimension of the permanent graphic, measured parallel to the longitudinal centerline, is desirably about 8 to about 9 centimeters.

The permanent and active graphics are suitably disposed on the outer cover. The term "disposed on," and variations thereof are intended to mean that one element can be integral with another element, or that one element can be a separate structure bonded to or placed with or placed near another element. Thus, the graphics can be formed or applied directly or indirectly to a surface of the outer cover, formed or applied between layers of a multiple layer outer cover, formed or applied to a substrate that is placed with or near the outer cover, formed or applied within a layer of the outer cover or another substrate, or other variations or combinations thereof. In particular embodiments, the graphics can be printed, sprayed, or otherwise applied directly on a layer of the outer cover. In other embodiments, the graphics can be applied to a layer placed with or near the outer cover, such as a substrate associated with the absorbent assembly, including but not limited to tissue layers, liquid handling layers, absorbent layers, or the like.

The permanent graphics can be located on the exterior surface of the outer cover to enhance the visual impact of the permanent graphics. Alternatively, however, the permanent graphics can be located on the interior surface of the outer cover or between layers of a multilayer outer cover, provided the permanent graphics remain visible from the exterior of the product.

The active graphics can be located on the interior surface of the outer cover, which is particularly desirable for active graphics that are triggered by urine in order to enhance the speed at which the graphics are contacted with urine and thus change their visual appearance. The outer cover desirably comprises a material that is formed or treated to be liquid impermeable. In alternative embodiments, the outer cover can comprise a material that is formed or treated to be at least partially liquid permeable. In this latter case, the active graphics can be located between layers of a multilayer outer cover, or, particularly for appearing graphics, on the exterior surface of the outer cover. Regardless of location, fading graphics should be visible from the exterior of the product before activation and appearing graphics should be visible from the exterior of the product after activation.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, can spread or be transported parallel to the plane of the liquid impermeable layer or laminate, but this is not considered to be within the meaning of "liquid impermeable" when used herein.

The outer cover can comprise a translucent material that has sufficient opacity, or a transparent or translucent material that is otherwise treated, to mask a urine soluble ink after it has dissolved. Such an outer cover should not be so opaque that the graphics printed on the interior surface of the outer cover or adjacent to the interior surface are obscured. Polymer films used to form the outer cover can be treated with titanium dioxide to make the film appear white and to develop sufficient opacity to mask urine, BM and dissolved inks. Examples of suitable outer cover materials include films formed of polyethylene, polypropylene, cataloy, bi-component, any polymer based extruded film, or the like. One such film is a polyethylene film having a thickness of about 0.2 millimeter (0.75 mil).

The permanent and active graphics can be formed on or applied to the outer cover or another substrate bonded to or placed with or placed near the outer cover by any suitable technique. The graphics are desirably registered with other components of the absorbent article during manufacture such that the graphics are positioned in the desired regions of the product.

For active graphics that are triggered by contact with urine, the active graphic can be in liquid communication with the absorbent assembly of the product. As used herein, the term "liquid communication" means that liquid such as urine is able to travel from one layer or element to another layer or element. The absorbent assembly can but need not include a slot or densified region, incorporate a liquid distribution layer, or the like, to channel or direct liquid to the location near the outer cover where the active graphics are located.

As noted previously, liquid soluble inks can be used to form the active graphics. It is theorized that migration of the dissolved inks away from the outer cover and into the absorbent assembly can improve the fading or disappearing quality of the active graphics. To enhance this effect, the outer cover can be attached to the absorbent assembly in a windowpane design, whereby the active graphic region of the outer cover is not bonded to the absorbent assembly and the regions of the outer cover surrounding the active graphic region are bonded to the absorbent assembly. One suitable method and apparatus for adhesively bonding the outer cover to the absorbent assembly in a windowpane design is disclosed in U.S. Pat. No. 5,683,752 issued Nov. 4, 1997 to Popp et al., which is incorporated herein by reference.

Absorbent articles suitable for use with the present invention include diapers, training pants, incontinence products, diaper pants, disposable underwear, or the like. Suitable training pants and diaper pants can have seamed side portions or refastenable side portions. The present invention is particularly suited for use with training pants or diaper pants to aid in toilet training. One particular training pant suitable for use with the present invention is disclosed in U.S. Pat. No. 4,940,464 issued Jul. 10, 1990 to Van Gompel et al., which is incorporated herein by reference. The Van Gompel et al. patent describes various materials of which the training pant can be made, and a method of constructing a training pant. The training pant can also be constructed using the methods and apparatus disclosed in U.S. Pat. No. 5,766,389 issued Jun. 16, 1998 to Brandon et al., which is also incorporated herein by reference.

The above-mentioned and other features and advantages of the present invention and the manner of attaining them will become more apparent, and the invention itself will be better understood by reference to the drawings and the following description of the drawings.

DETAILED DESCRIPTION OF THE DRAWINGS

The principles of the present invention can be incorporated into a variety of absorbent articles, and particularly disposable absorbent articles. The term "disposable" refers to articles which are designed to be discarded after a limited use rather than being laundered or otherwise restored for reuse. For ease of explanation, the description hereafter will be in terms of a child's training pant.

Figure 1:
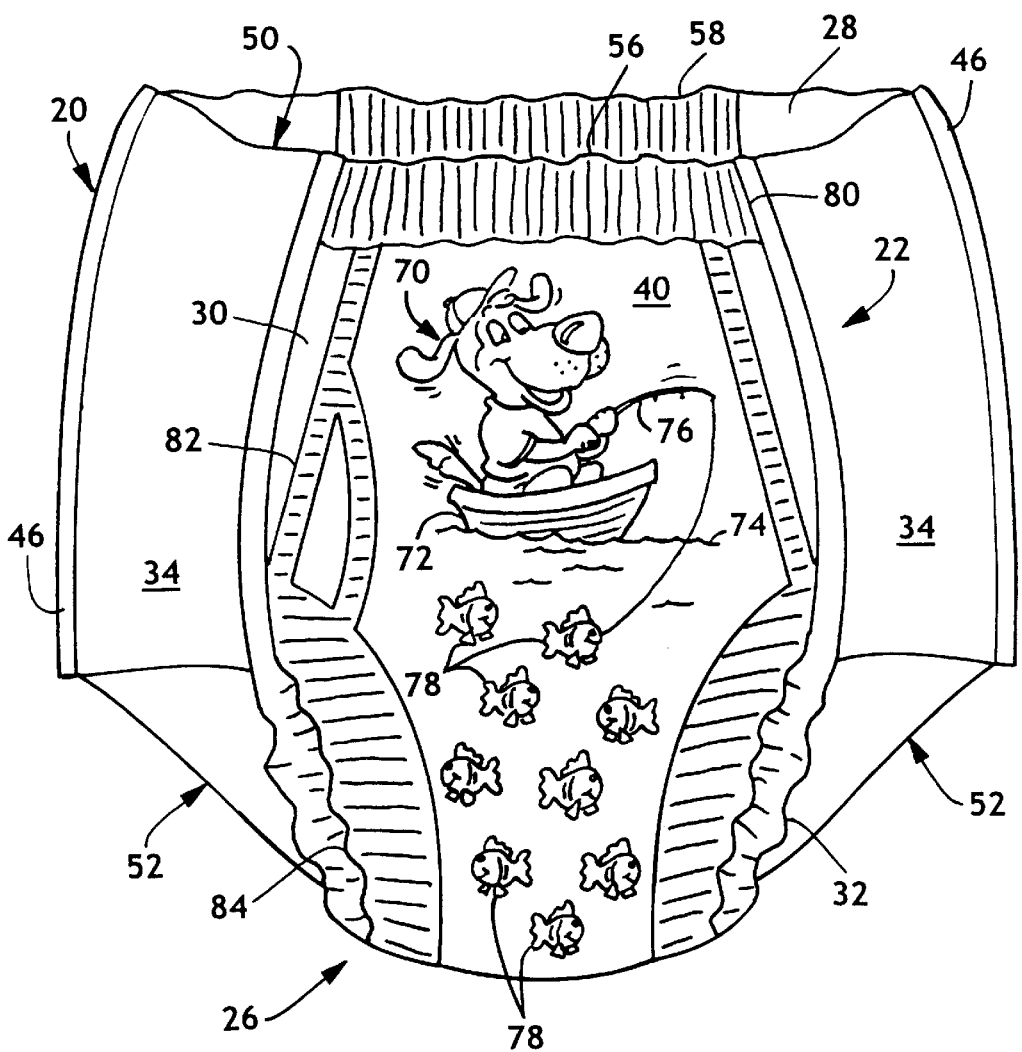
FIG. 1 illustrates a front perspective view of a training pant incorporating the principles of the present invention, showing both permanent graphics and active graphics.
Figure 2:
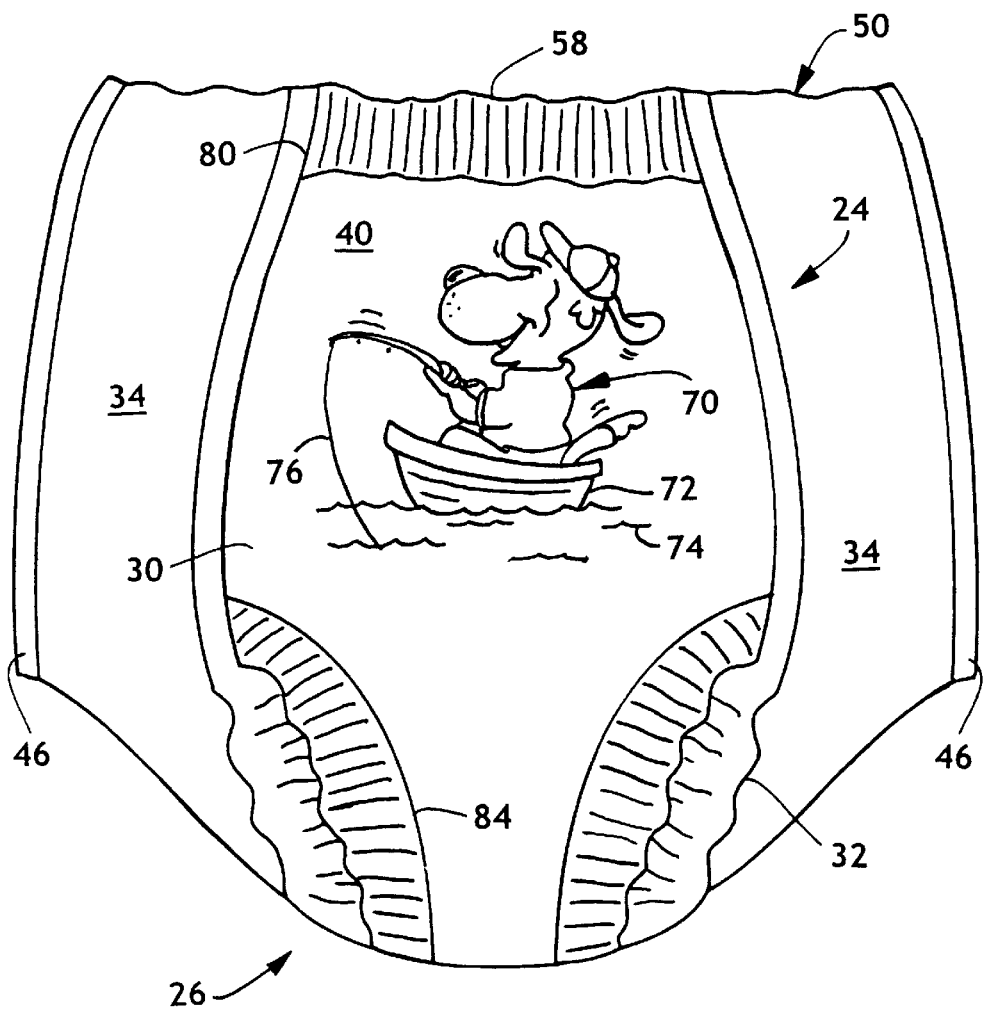
FIG. 2 illustrates a rear perspective view of the training pant of FIG. 1.
Figure 3:
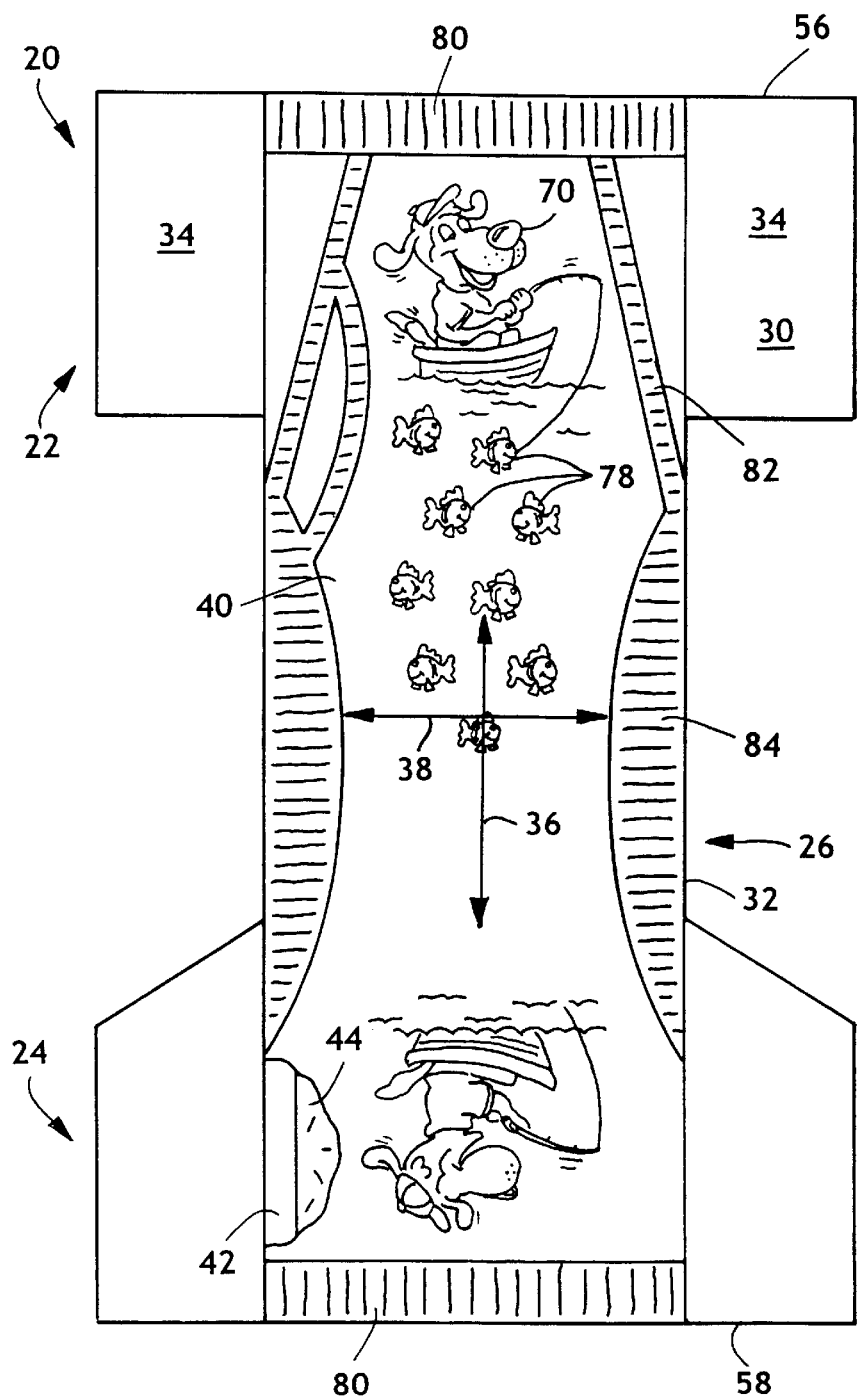
FIG. 3 illustrates a top plan, partially disassembled view of the training pant of FIGS. 1 and 2, in a stretched and laid flat condition and with portions broken away for purposes of illustration.

A training pant 20 is illustrated in a fully assembled condition in FIGS. 1 and 2 and in a partially disassembled, stretched and laid flat condition in FIG. 3. The training pant 20 defines a first or front waist region 22, a second or back waist region 24, a crotch region 26 positioned between and interconnecting the front and back waist regions, an inner surface 28 (FIG. 1) which is configured to contact the wearer, and an outer surface 30 opposite the inner surface which is configured to contact the wearer's clothing. The illustrated training pant 20 comprises an absorbent chassis 32 and a plurality of transversely opposed side panels 34. The absorbent chassis 32 and side panels 34 can be integrally formed or comprise two or more separate elements, as shown.

The training pant 20 defines a longitudinal centerline 36 (FIG. 3), a transverse centerline 38 (FIG. 3), a first or front longitudinal end edge 56, and a second or back longitudinal end edge 58. The first waist region 22 abuts the first longitudinal end edge 56, and the second waist region 24 abuts the second longitudinal end edge 58. "Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

The illustrated absorbent chassis 32 comprises an outer cover 40 and a bodyside liner 42 (FIG. 3) which is connected to the outer cover in a superposed relation. The absorbent chassis 32 also comprises an absorbent assembly 44 (FIG. 3) which is located between the outer cover and the bodyside liner, and can optionally include a pair of containment flaps (not shown).

With the training pant 20 in a fully assembled condition as illustrated in FIGS. 1 and 2, the front and back waist regions 22 and 24 are joined together by side seams 46 to define a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer.

The longitudinal end edges 56 and 58 of the training pant 20 are configured to encircle the waist of the wearer when worn and provide the waist opening 50.

The absorbent chassis 32 is configured to contain and/or absorb any body exudates discharged from the wearer. For example, the absorbent chassis 32 desirably although not necessarily comprises the pair of containment flaps (not shown) which can be configured to provide a barrier to the transverse flow of body exudates. Suitable constructions and arrangements for the containment flaps are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include a front waist elastic member, a rear waist elastic member, and leg elastic members (not shown), as are known to those skilled in the art. Waist elastic members and leg elastic members can be operatively joined to the outer cover 40 and/or bodyside liner 42 of the training pant 20. Elastic members for the containment flaps, waist elastics and leg elastics can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members comprise a plurality of dry-spun coalesced multifilament spandex elastomeric threads sold under the trade name LYCRA® and available from E. I. Du Pont de Nemours and Company, Wilmington, Del.

The outer cover 40 has an exterior surface corresponding to the outer surface 30 of the training pant and an opposite interior surface. The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., or from National Starch and Chemical Company, Bridgewater, N.J. The liquid permeable outer layer can be any suitable material and desirably one that provides a generally cloth-like texture. One example of such a material is a 20 gsm (grams per square meter) spunbond polypropylene nonwoven web. The outer layer can also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials can also be used. The inner layer, or the liquid impermeable outer cover 40 when a single layer, prevents waste material from wetting articles, such as bed-sheets and clothing, as well as the wearer and caregiver. A suitable liquid impermeable film for use as liquid impermeable inner layer, or a single layer liquid impermeable outer cover 40, is a 0.02 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

As shown in FIGS. 1–3, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young boys, includes registered outer cover graphics, including interactive wetness indicating graphics. More specifically, the training pant includes a permanent character graphic 70 in the form of a dog having human-like expressions and wearing a shirt and a hat, permanent object graphics 72, 74 and 76 in the form of a boat, curved line segments denoting the surface of water, and a fishing pole, respectively, and a plurality of active object graphics 78 representing fish. The outer cover graphics also include a simulated elastic waistband 80, a simulated fly opening 82, and simulated elastic leg bands 84, all of which can be permanent graphics.

The active object graphics 78 comprise a moisture sensitive color change composition and are in liquid communication with the absorbent assembly 44. In the illustrated embodiment, the active object graphics 78 are disposed on the interior surface of the outer cover 40 and are visible from the exterior surface of the outer cover. When the child wets the training pant 20, liquid is communicated to the active object graphics 78, whereupon the object graphics change color from a pre-activation color to a post-activation color.

To create the effect of the active object graphics 78 disappearing, the preactivation color of the active object graphics is substantially different from the color of the outer cover, and the post-activation color of the active object graphics is clear or substantially the same as the color of the outer cover. The color of the outer cover may differ in various places, although it is the color surrounding the active object graphics 78 that is important for purposes of the ability to view the active object graphics. In many current commercial absorbent articles, the outer cover is white in color. Thus, in one particular embodiment the post-activation color is white or clear. By way of illustration, the active object graphics 78 can comprise a moisture sensitive color change composition that has a pre-activation color of blue or red and a post-activation color of white or clear.

Figure 4:
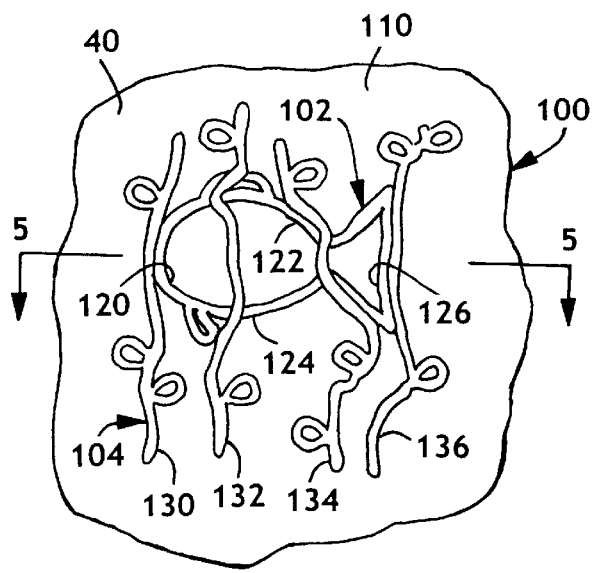
FIG. 4 representatively shows an enlarged top plan view of a portion of an outer cover of an alternative training pant, viewed from an exterior surface.
Figure 5:
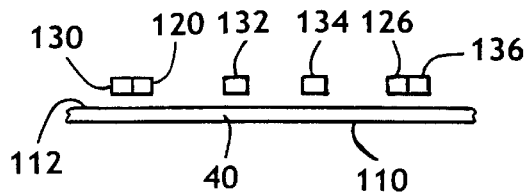
FIG. 5 illustrates an exploded section view of the outer cover taken from the plane of the line 5—5 in FIG. 4, again with the various components shown enlarged from actual size for purposes of illustration.

A portion of an outer cover 40 of an alternative training pant 100 is shown separately in FIGS. 4 and 5. The training pant 100 includes an active object graphic 102 in the form of a fish and a permanent background graphic 104 in the form of weeds. The outer cover 40 has an exterior surface 110 and an opposite interior surface 112, where the plan view of FIG. 4 is from the perspective of the exterior surface. The illustrated outer cover 40 consists of a single layer. Alternatively, however, the outer cover can comprise a multi-layer composite (not shown) where the layers are bonded together by adhesives, thermal bonds, ultrasonic bonds, or other suitable means.

The active and permanent graphics 102 and 104 can be disposed on the outer cover 40, which includes, in particular, on the exterior surface 110, on the interior surface 112, between layers of a multi-layer composite, on either or both facing surfaces of a layered composite, on the surface of the absorbent assembly 44 that faces the outer cover, or between the absorbent assembly and the outer cover. The outer cover 40 is desirably formed of a material that is liquid impermeable, in which case the active graphic 102 is disposed on the interior surface 112 of the outer cover 40, as illustrated, on the surface of the absorbent assembly 44 that faces the outer cover, or between the absorbent assembly and the outer cover. The active and permanent graphics 102 and 104 need not be located in the same position or on the same substrate. In the illustrated embodiment, the permanent graphic 104 is positioned on the interior surface 112 of the outer cover 40.

Figure 6:
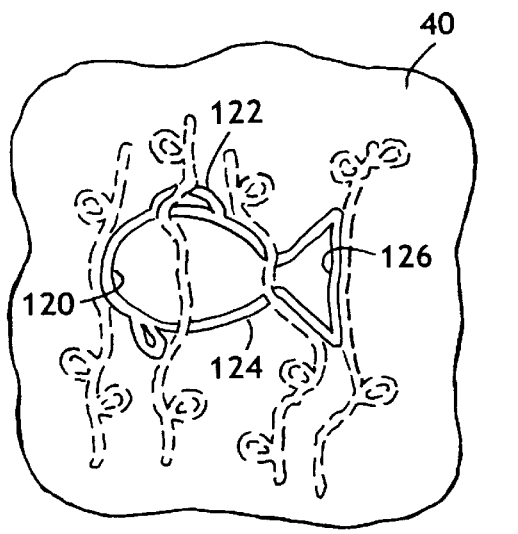
FIG. 6 highlights certain active graphics shown in FIG. 4.
Figure 7:
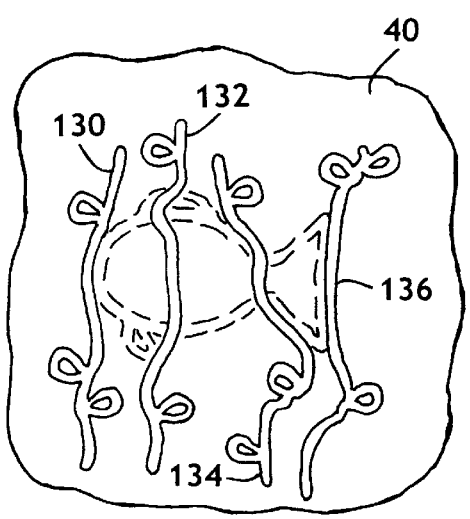
FIG. 7 highlights certain background graphics shown in FIG. 4.

In the embodiment illustrated in FIGS. 4 and 5, the active graphic 102 comprises the outline of an image of a fish. The fish 102 is formed by a plurality of closely spaced but non-continuous line segments 120, 122, 124 and 126. The active fish graphic 102 is shown more clearly in FIG. 6, where the permanent graphic 104 is shown with phantom lines. The permanent graphic 104 comprises a variety of weeds formed by a plurality of line segments 130, 132, 134 and 136. The permanent weed graphic 104 is shown more clearly in FIG. 7, where the active fish graphic 102 is shown with phantom lines.

The active and permanent graphics 102 and 104 are suitably formed to have different colors than the outer cover 40. For example, the outer cover 40 can be white, the permanent weeds 104 can be green, and the pre-activation fish 102 can be red. Post-activation, the line segments forming the fish 102 can be white or clear so that they are no longer visible, or they can be green so that they blend in with the weeds 104 and are no longer separately identifiable as fish. Desirably, as illustrated, the line segments 120, 122, 124 and 126 that define the outline of the fish 102 and the line segments 130, 132, 134 and 136 that define the weeds 104 are compatible with one another. For example, the dorsal and pectoral fins on the fish are similar to the leaves on the weeds 104. Also, portions of the line segments for the fish and the weed extend side-by-side for limited distances. The background graphics can of course comprise multiple objects and colors, although the color of the background graphics near and/or surrounding the active graphics will impact the degree to which the active graphic seems to appear or disappear.

In particular embodiments, a second active graphic is applied over the first active fish graphic 102. The second active graphic comprises a moisture sensitive color change composition that has a pre-activation color of white or clear and a post-activation color that is the same as the permanent weed graphics 104. The overprinting of the second active graphic would desirably be in the same pattern as the weeds 104, in order to further break-up the color changing objects and help camouflage the active fish graphic 102.

Figure 8:
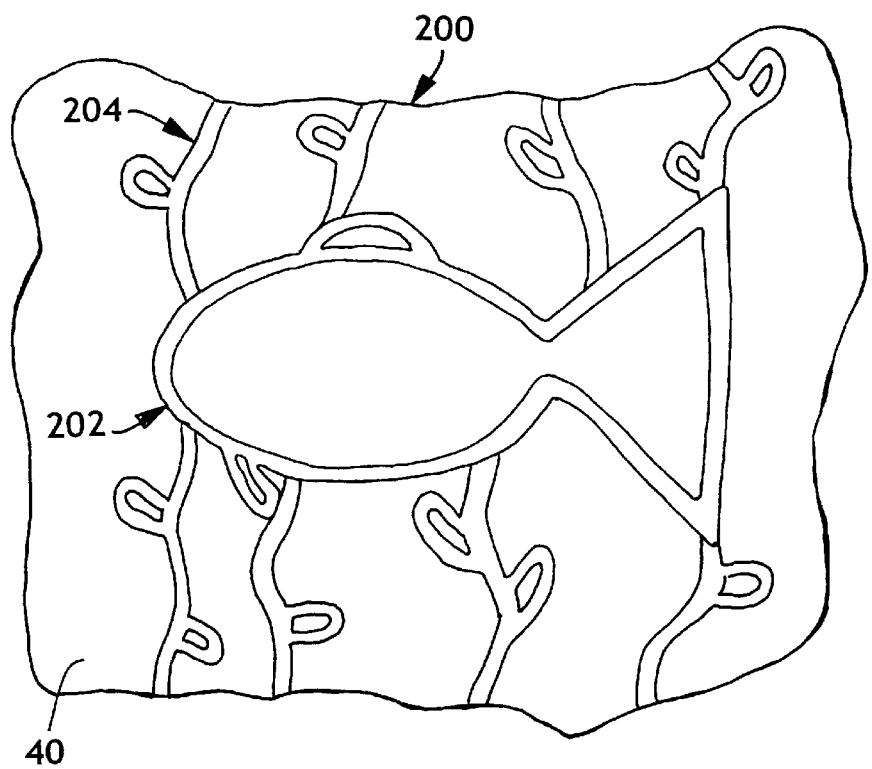
FIG. 8 representatively shows an enlarged top plan view of a portion of an outer cover of another alternative training pant, also viewed from an exterior surface.
Figure 9:
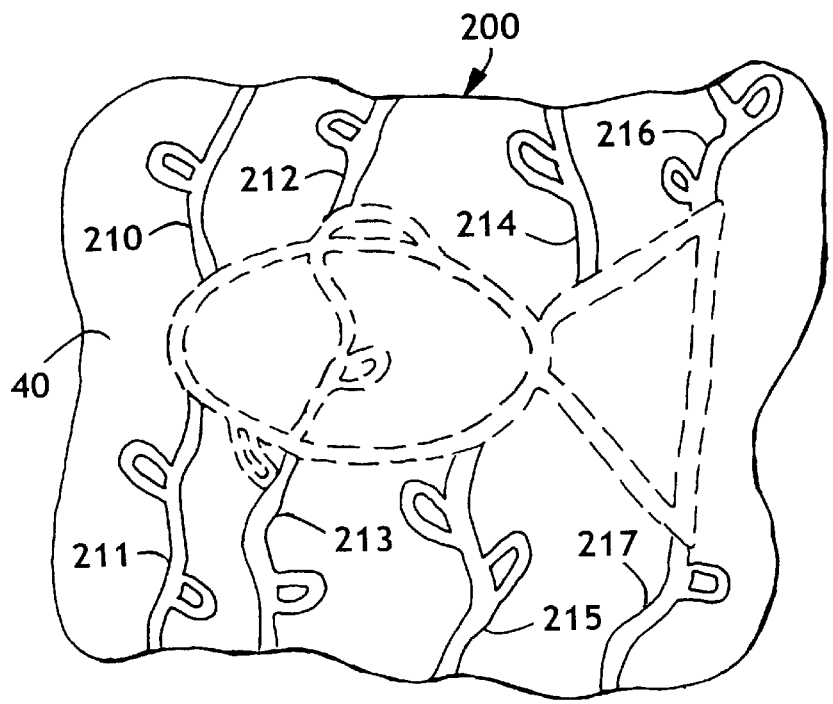
FIGS. 9–13 highlight certain portions of the graphics shown in FIG. 8.

FIG. 8 illustrates a portion of an outer cover 40 of another alternative training pant 200. FIG. 8 represents the pre-activation condition of the outer cover graphics. The training pant 200 includes an active object graphic 202 in the form of a fish and a permanent background graphic 204 in the form of weeds. Continuing with the same color example, the outer cover 40 can be white, the permanent weeds 104 can be green, and the pre-activation fish 102 can be red. The line segments which form permanent portions of the weeds 204 are shown separately in FIG. 9 and are identified with reference numerals 210–217.

Figure 10:
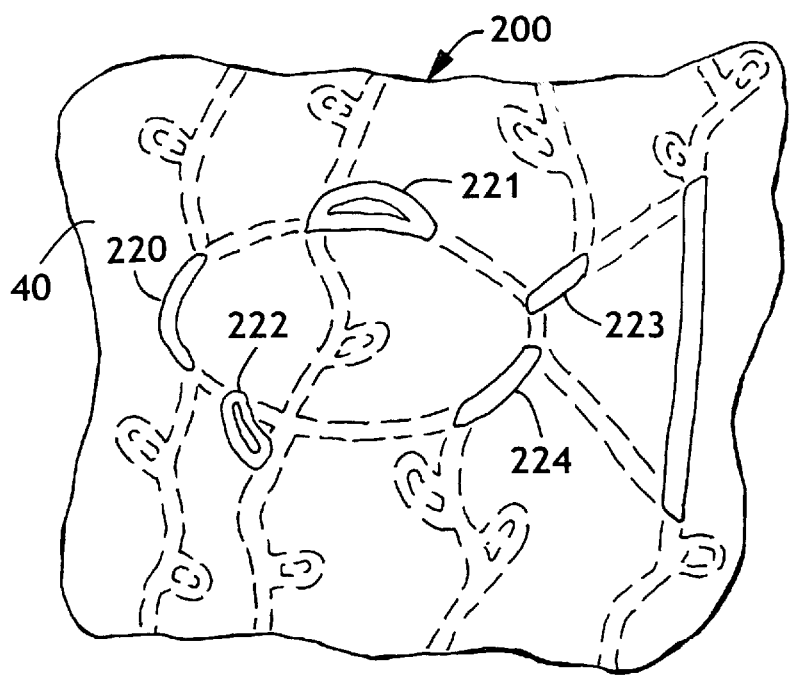
Figure 11:
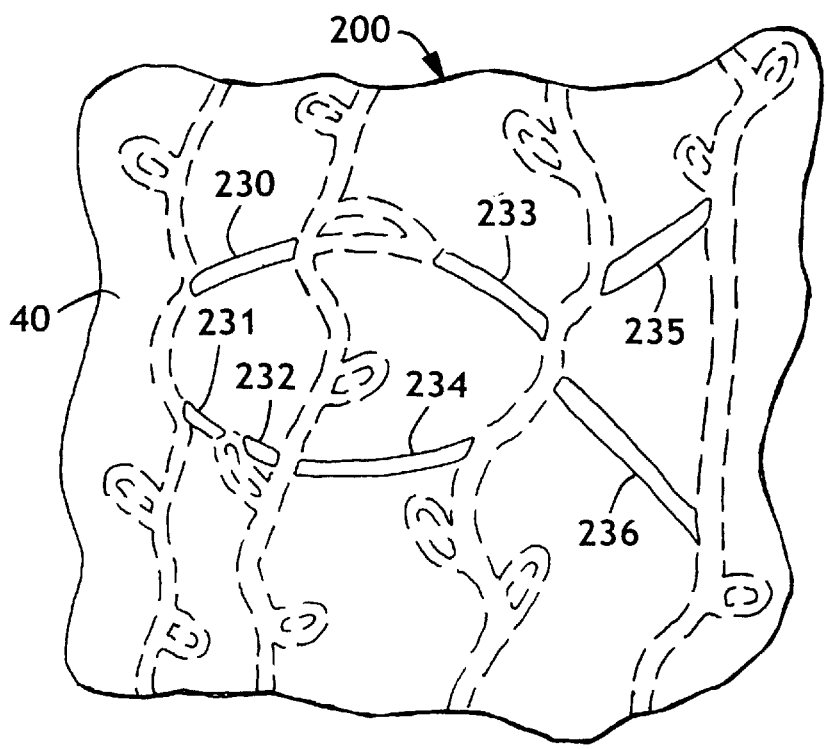
Figure 12:
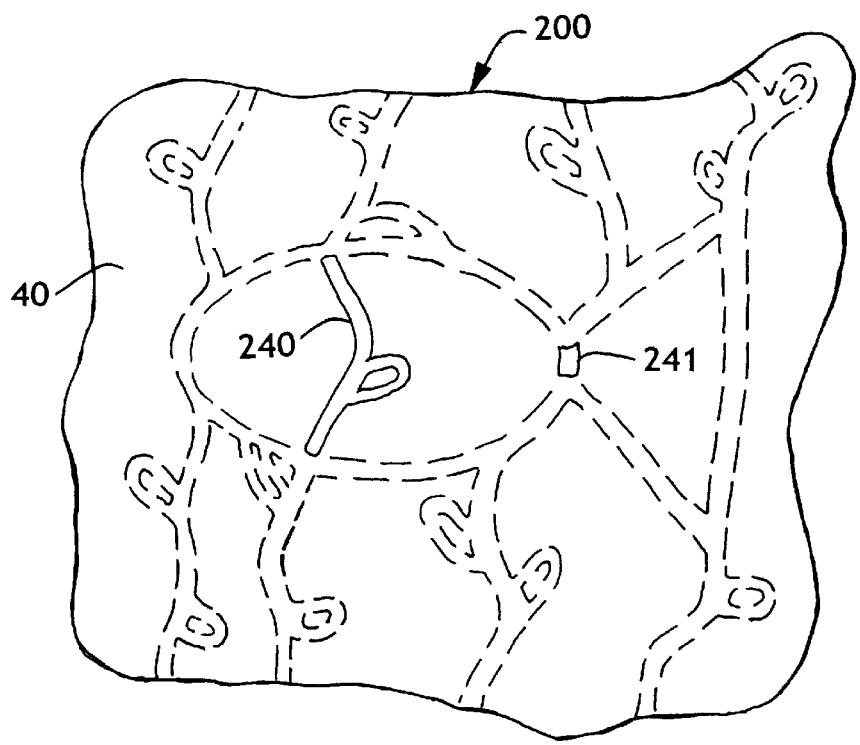

In this embodiment, some of the line segments that form the fish 102 have a post-activation color of green and fill in portions of the picture of the weeds. These line segments are identified with reference numerals 220–224 and are shown separately in FIG. 10. Also in this embodiment, other portions of the line segments that form the fish 102 have a post-activation color of white or clear so that they are no longer visible after activation. These line segments are identified with reference numerals 230–236 and are shown separately in FIG. 11. Furthermore, certain line segments used in the outer cover graphics have a preactivation color of white or clear and a post-activation color of green. In this way, these line segments, which are identified with reference numerals 240 and 241 and are shown separately in FIG. 12, are not seen prior to activation and fill in portions of the picture of the weeds after activation.

Figure 13:
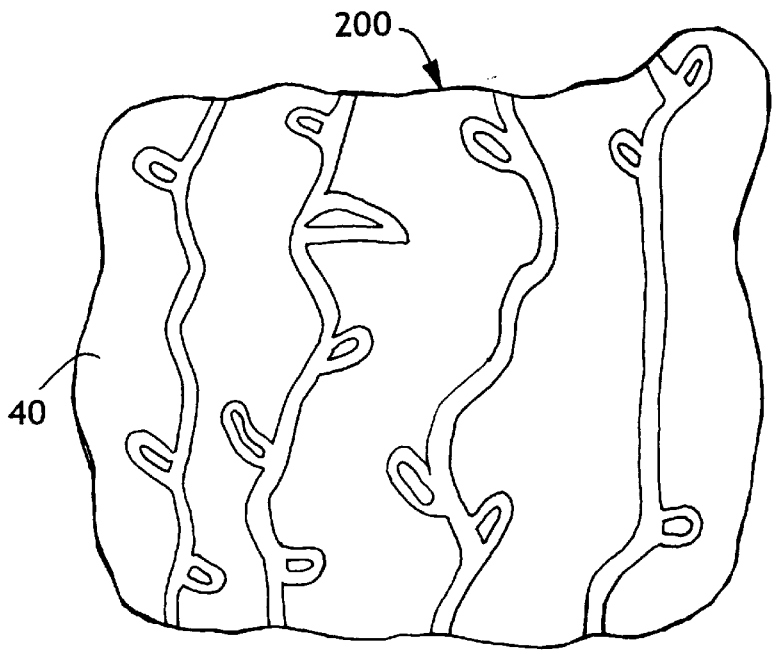

Post-activation, the outer graphics appear as illustrated in FIG. 13. The picture of the weeds is comprised after activation of the permanent graphic line segments 210–217 (FIG. 9), portions of the original fish graphic line segments 220–224 (FIG. 10), and the appearing line segments 240 and 241 (FIG. 12). The fish is not visible after activation.

The liquid permeable bodyside liner 42 generally overlies the outer cover 40 and absorbent assembly 44, and can but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, vailable from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly. The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has a side panel 34 disposed on each side of the absorbent chassis 32. In the illustrated embodiment, the pair of transversely opposed side panels 34 are permanently bonded to the absorbent chassis 32 and permanently bonded to one another, using attachment means known to those skilled in the art such as adhesive, thermal or ultrasonic bonding.

The side panels 34 desirably comprise an elastic material capable of stretching in a direction parallel to the transverse axis 49 of the training pant 20. Suitable elastic materials, as well as one described process of incorporating elastic side panels into a training pant, are described in the following U.S. Patants: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material can comprise other woven or nonwoven materials, such as those described above as being suitable for the outer cover 40 or bodyside liner 42.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent article comprising:

an outer cover having an interior surface, an opposite exterior surface and a first color;

an absorbent assembly disposed on the interior surface; and an active graphic disposed on the outer cover and comprising a color change composition, the active graphic having a pre-activation color different from the first color and a post-activation color substantially the same as the first color.

2. An absorbent article comprising:

an outer cover having an interior surface, an opposite exterior surface and a first color;

an absorbent assembly disposed on the interior surface;

an active graphic disposed on the outer cover and comprising a color change composition; and a background graphic disposed on the outer cover and having a second color different from the first color;

wherein the active graphic has a pre-activation color different from the first color and the second color and a post-activation color substantially the same as the second color.

3. The absorbent article of claim 2, wherein the active graphic comprises at least two color change compositions, the active graphic having a pre-activation color different from the first color and the second color, at least one of the color change compositions having a post-activation color substantially the same as the first color and at least one of the color change compositions having a post-activation color substantially the same as the second color.

4. The absorbent article of claim 2, wherein the active graphic comprises first and second active graphics disposed on the outer cover and comprising color change compositions, the first active graphic having a pre-activation color different from the first color and the second color and a post-activation color substantially the same as the second color; the second active graphic having a pre-activation color substantially the same as the first color and a post-activation color substantially the same as the second color.

5. The absorbent article of claim 2, wherein the background graphic comprises a permanent graphic.

6. The absorbent article of claim 1, comprising 3 or more active graphics.

7. The absorbent article of claim 6, wherein the active graphics have a size of at least about 1.5 by 1.5 centimeter and less than about 3 by 3 centimeters.

8. The absorbent article of claim 1, wherein the first color is white.

9. An absorbent article comprising:

an outer cover having an interior surface, an opposite exterior surface and a first color;

an absorbent assembly disposed on the interior surface; and an active graphic disposed on the outer cover and comprising a moisture sensitive color change composition, the active graphic having a pre-activation color different from the first color and a post-activation color substantially the same as the first color.

10. An absorbent article comprising:
an outer cover having an interior surface, an opposite exterior surface and a first color;
an absorbent assembly disposed on the interior surface;
an active graphic disposed on the outer cover and comprising a moisture sensitive color change composition; and
a background graphic disposed on the outer cover and having a second color different from the first color;
wherein the active graphic has a pre-activation color different from the first color and the second color and a post-activation color substantially the same as the second color.

11. The absorbent article of claim 10, wherein the active graphic comprises at least two moisture sensitive color change compositions, the active graphic having a pre-activation color different from the first color and the second color, at least one of the moisture sensitive color change compositions having a post-activation color substantially the same as the first color and at least one of the moisture sensitive color change compositions having a post-activation color substantially the same as the second color.

12. The absorbent article of claim 10, wherein the active graphic comprises first and second active graphics disposed on the outer cover and comprising moisture sensitive color change compositions, the first active graphic having a pre-activation color different from the first color and the second color and a post-activation color substantially the same as the second color, the second active graphic having a pre-activation color substantially the same as the first color and a post-activation color substantially the same as the second color.

13. The absorbent article of claim 10, wherein the background graphic comprises a permanent graphic.

14. The absorbent article of claim 11, wherein the active graphic is disposed on the interior surface of the outer cover.

15. The absorbent article of claim 9, wherein the active graphic comprises a plurality of line segments.

16. The absorbent article of claim 15, wherein the line segments have a width of from about 1 to about 2 millimeters.

17. A disposable absorbent article defining first and second waist regions and a crotch region disposed between and interconnecting the waist regions, comprising:
an outer cover formed of a substantially liquid impermeable material and having an interior surface, an opposite exterior surface and a first color;
a bodyside liner connected to the outer cover in a superposed relation;
an absorbent assembly located between the outer cover and the bodyside liner and disposed on the interior surface of the outer cover;
a permanent background graphic disposed on the outer cover and having a second color different from the first color; and
at least three active graphics disposed on the outer cover and in liquid communication with the absorbent assembly, the at least three active graphics comprising a moisture sensitive color change composition, at least one of the active graphics having a pre-activation color different from the first color and the second color and a post-activation color substantially the same as the second color.

18. A disposable absorbent article defining first and second waist regions and a crotch region disposed between and interconnecting the waist regions, comprising:
an outer cover formed of a substantially liquid impermeable material and having an interior surface, an opposite exterior surface and a first color;
a bodyside liner connected to the outer cover in a superposed relation;
an absorbent assembly located between the outer cover and the bodyside liner and disposed on the interior surface of the outer cover;
a permanent background graphic disposed on the outer cover and having a second color different from the first color; and
at least three active graphics disposed on the outer cover and in liquid communication with the absorbent assembly, the at least three active graphics comprising a moisture sensitive color change composition, at least one of the active graphics having a pre-activation color different from the first color and the second color and a post-activation color substantially the same as the first color.

19. A disposable absorbent article comprising:
an outer cover having an interior surface, an opposite exterior surface and a first color;
an absorbent assembly disposed on the interior surface; and
an active graphic disposed on the outer cover and comprising a color change composition, the active graphic having a pre-activation color different from the first color. and a post-activation color substantially the same as the first color.

20. A disposable absorbent article comprising:
an outer cover having an interior surface, an opposite exterior surface and a first color;
an absorbent assembly disposed on the interior surface;
an active graphic disposed on the outer cover and comprising a color change composition; and
a background graphic disposed on the outer cover and having a second color different from the first color;
wherein the active graphic has a pre-activation color different from the first color and the second color and a post-activation color substantially the same as the second color.

21. The absorbent article of claim 20, wherein the active graphic comprises at least two color change compositions, the active graphic having a pre-activation color different from the first color and the second color, at least one of the color change compositions having a post-activation color substantially the same as the first color and at least one of the color change compositions having a post-activation color substantially the same as the second color.

22. The absorbent article of claim 20, wherein the active graphic comprises first and second active graphics disposed on the outer cover and comprising color change compositions, the first active graphic having a pre-activation color different from the first color and the second color and a post-activation color substantially the same as the second color; the second active graphic having a pre-activation color substantially the same as the first color and a post-activation color substantially the same as the second color.

23. The absorbent article of claim 20, wherein the background graphic comprises a permanent graphic.

24. The absorbent article of claim 19, comprising 3 or more active graphics.

25. The absorbent article of claim 24, wherein the active graphics have a size of at least about 1.5 by 1.5 centimeter and less than about 3 by 3 centimeters.

26. The absorbent article of claim 19, wherein the first color is white.

* * * * *